United States Patent
Bie et al.

(10) Patent No.: US 12,168,091 B2
(45) Date of Patent: Dec. 17, 2024

(54) ATOMIZER AND LIQUID STORAGE ASSEMBLY THEREOF, AND ELECTRONIC ATOMIZING DEVICE

(71) Applicant: Shenzhen Smoore Technology Limited, Shenzhen (CN)

(72) Inventors: Chaoyong Bie, Shenzhen (CN); Haidong Zhu, Shenzhen (CN); Aping Zhou, Shenzhen (CN); Yisong Wei, Shenzhen (CN); Wei Li, Shenzhen (CN); Zhong Luo, Shenzhen (CN)

(73) Assignee: SHENZHEN SMOORE TECHNOLOGY LIMITED, Shenzhen (CN)

(*) Notice: Subject to any disclaimer, the term of this patent is extended or adjusted under 35 U.S.C. 154(b) by 722 days.

(21) Appl. No.: 17/237,062

(22) Filed: Apr. 22, 2021

(65) Prior Publication Data

US 2021/0386941 A1 Dec. 16, 2021

(30) Foreign Application Priority Data

Jun. 15, 2020 (CN) .......................... 202010545006.2

(51) Int. Cl.
*A61M 11/04* (2006.01)
*A24F 40/40* (2020.01)
(Continued)

(52) U.S. Cl.
CPC ........... *A61M 11/042* (2014.02); *A24F 40/40* (2020.01); *A61M 15/0086* (2013.01); *A61M 15/06* (2013.01)

(58) Field of Classification Search
CPC .... A61M 11/00; A61M 11/04; A61M 11/042; A61M 11/06; A61M 11/08; A61M 15/00;
(Continued)

(56) References Cited

U.S. PATENT DOCUMENTS 8,707,965 B2 * 4/2014 Newton ................ A24F 40/485
131/194
2011/0011396 A1 * 1/2011 Fang .................... A61M 11/041
128/202.21
(Continued)

FOREIGN PATENT DOCUMENTS

CN 104509986 A 4/2015
CN 205848684 U 1/2017
(Continued)

OTHER PUBLICATIONS

European search report,European Application No. 21179414.4, mailed Nov. 21, 2021 (7 pages).
(Continued)

*Primary Examiner* — Colin W Stuart

(57) ABSTRACT

An atomizer, a liquid storage assembly thereof and an electron atomizing device are disclosed. The atomizer includes an atomizing core assembly having a liquid inlet. The liquid storage assembly includes a housing defining a liquid storage cavity and a first assembling hole, wherein the first assembling hole is configured to receive an end of an atomizing core assembly; an inner wall arranged in the liquid storage cavity, configured to sleeve around the atomizing core assembly, wherein a capillary gap is defined between the inner wall and an outer wall of the atomizing core assembly, and the capillary gap is configured to guide liquid in the liquid storage cavity to pass through the liquid inlet.

20 Claims, 9 Drawing Sheets

(51) Int. Cl.
*A61M 15/00* (2006.01)
*A61M 15/06* (2006.01)

(58) Field of Classification Search
CPC ... A61M 15/0001; A61M 15/06; A24F 40/40; A24F 40/44; A24F 40/46; A24F 42/00
See application file for complete search history.

(56) References Cited

U.S. PATENT DOCUMENTS

| | | | | |
|---|---|---|---|---|
| 2015/0020822 | A1* | 1/2015 | Janardhan | A61M 15/06 131/328 |
| 2017/0064997 | A1* | 3/2017 | Murison | A24F 40/53 |
| 2017/0367402 | A1* | 12/2017 | Lau | A24F 40/485 |
| 2018/0303160 | A1* | 10/2018 | Davis | A24F 40/48 |
| 2019/0124990 | A1 | 5/2019 | Qiu | |
| 2020/0345069 | A1* | 11/2020 | Potter | A24F 40/46 |
| 2021/0227882 | A1* | 7/2021 | Hijma | H05B 1/0297 |
| 2021/0337878 | A1* | 11/2021 | Gretton | A24F 40/10 |
| 2022/0192271 | A1* | 6/2022 | Wen | A24F 40/40 |
| 2022/0378098 | A1* | 12/2022 | Kleine-Wächter | A24F 40/10 |

FOREIGN PATENT DOCUMENTS

| | | | |
|---|---|---|---|
| CN | 109259325 | A | 1/2019 |
| CN | 208370945 | U | 1/2019 |
| CN | 110236233 | A | 9/2019 |
| CN | 110250576 | A | 9/2019 |
| CN | 110638102 | A | 1/2020 |
| CN | 210017880 | U | 2/2020 |
| CN | 111011933 | A | 4/2020 |
| CN | 210329352 | U | 4/2020 |
| CN | 111165880 | A | 5/2020 |
| CN | 211091889 | U | 7/2020 |
| CN | 212545554 | U | 2/2021 |
| DE | 102019124411 | A1 * | 3/2021 ............ A24F 40/10 |
| WO | WO2019207010 | A1 | 10/2019 |

OTHER PUBLICATIONS

Chinese Notification to Grant Patent Right for Invention, Chinese Application No. 202010545006.2, mailed Sep. 30, 2024 (6 pages).

* cited by examiner

ATOMIZER AND LIQUID STORAGE ASSEMBLY THEREOF, AND ELECTRONIC ATOMIZING DEVICE

CROSS-REFERENCE TO RELATED APPLICATIONS

The present application claims priority of Chinese Patent Application No. 202010545006.2, filed on Jun. 15, 2020, in the National Intellectual Property Administration of China, the entire contents of which are hereby incorporated by reference in its entirety.

TECHNICAL FIELD

The disclosure relates to the technical field of atomizing, in particular to an atomizer and a liquid storage assembly thereof and an electronic atomizing device.

BACKGROUND

In the related art, an electronic atomizing device mainly includes an atomizer and a body component. The atomizer generally comprises a liquid storage cavity and an atomizing assembly, wherein the liquid storage cavity is used for storing an atomizable medium, and the atomizing assembly is used for heating and atomizing the atomizable medium to form smoke which can be inhaled by a smoker. The body component is used to provide energy to the atomizer.

A position of an oil inlet of the atomizing core is generally arranged in the middle of the atomizing core or at the upper end of the atomizing core. When the liquid level of the e-liquid is lower than the position of the oil inlet, the e-liquid below the oil inlet cannot enter the atomizing core, and the atomizing core will be easily burnt.

SUMMARY OF THE DISCLOSURE

A liquid storage assembly for an atomizer may be provided. The liquid storage assembly may include a housing and an inner wall. The housing may define a liquid storage cavity and a first assembling hole, the first assembling hole is configured to receive an end of an atomizing core assembly. The inner wall may be arranged in the liquid storage cavity, wherein a capillary gap is defined between the inner wall and an outer wall of the atomizing core assembly, and the capillary gap is configured to guide liquid in the liquid storage cavity to pass through the liquid inlet.

An atomizer is provided. The atomizer may include an atomizing core assembly defining a liquid inlet and a liquid storage assembly The liquid storage assembly may include a housing defining a liquid storage cavity and an inner wall arranged in the liquid storage cavity; the atomizing core assembly is arranged in the liquid storage cavity, and the inner wall is arranged around the atomizing core assembly; a capillary gap is defined between the inner wall and an outer wall of the atomizing core assembly; when liquid level in the liquid storage cavity is lower than the position of the liquid inlet, liquid in the liquid storage cavity enters the liquid inlet along the capillary gap.

An electronic atomizing device is provided. The electronic atomizing device may include a body component and an atomizer. The atomizer may include an atomizing core assembly defining a liquid inlet and a liquid storage assembly including a housing defining a liquid storage cavity, and an inner wall arranged in the liquid storage cavity. The atomizing core assembly is arranged in the liquid storage cavity, and the inner wall is arranged around the atomizing core assembly. A capillary gap is defined between the inner wall and an outer wall of the atomizing core assembly. When liquid level in the liquid storage cavity is lower than the position of the liquid inlet, liquid in the liquid storage cavity enters the liquid inlet along the capillary gap. The body component is electrically connected to the atomizer to supply power to the atomizer.

BRIEF DESCRIPTION OF THE DRAWINGS

In order to describe the technical solutions of the specific embodiments of the present disclosure more clearly, the drawings used in the description of the embodiments of the present disclosure will be briefly introduced below. Obviously, the following drawings are only some embodiments of the present disclosure. To any one of skill in the art, other drawings may be obtained without any creative work based on the following drawings.

DETAILED DESCRIPTION

In order to make the technical solution described in embodiments or background of the present disclosure more clearly, the drawings used for the description of the embodiments or background will be described. Obviously, the following drawings are only some embodiments of the present disclosure. To any one of skill in the art, other drawings may be obtained without any creative work based on the following drawings.

The terms "first", "second" and "second" are for descriptive purposes only and are not to be construed as indicating or implying relative importance or implicitly specifying the number of technical features indicated. Thus, the features defined with "first", "second" and "second" may explicitly or implicitly include one or more of the described features.

In the description of the present disclosure, "plurality" means two or more, unless otherwise expressly and specifically limited. In addition, the terms "including" and "having" and any variations thereof are intended to cover non-exclusive inclusion. For example, a process, method, system, product, or device that includes a series of operations or units is not limited to the listed operations or units, but optionally includes unlisted operations or units, or optionally also includes other operations or units inherent to these processes, methods, products or equipment.

Reference term "embodiment" means that a particular feature, structure, or characteristic described in connection with the embodiment or example is included in at least one embodiment or example of the present disclosure. The illustrative descriptions of the terms throughout this specification are not necessarily referring to the same embodiment or example of the present disclosure, nor are separate or alternative embodiments mutually exclusive with other embodiments. In addition, one skilled in the art may combine the different embodiments or examples described in this specification and features of different embodiments or examples without conflicting with each other.

Figure 1:
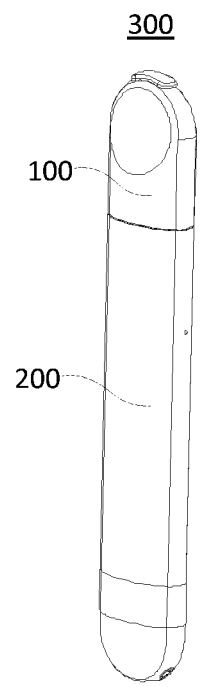
FIG. 1 is a structural schematic view of an electronic atomizer according to an embodiment of the present disclosure.
Figure 2:
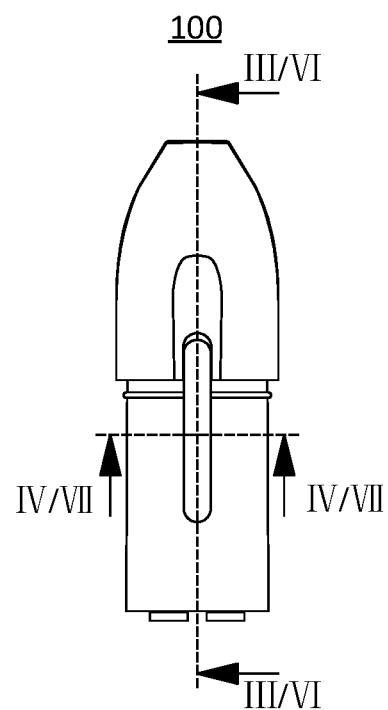
FIG. 2 is a lateral structural schematic view of an atomizer of the electronic atomizing device in FIG. 1.
Figure 3:
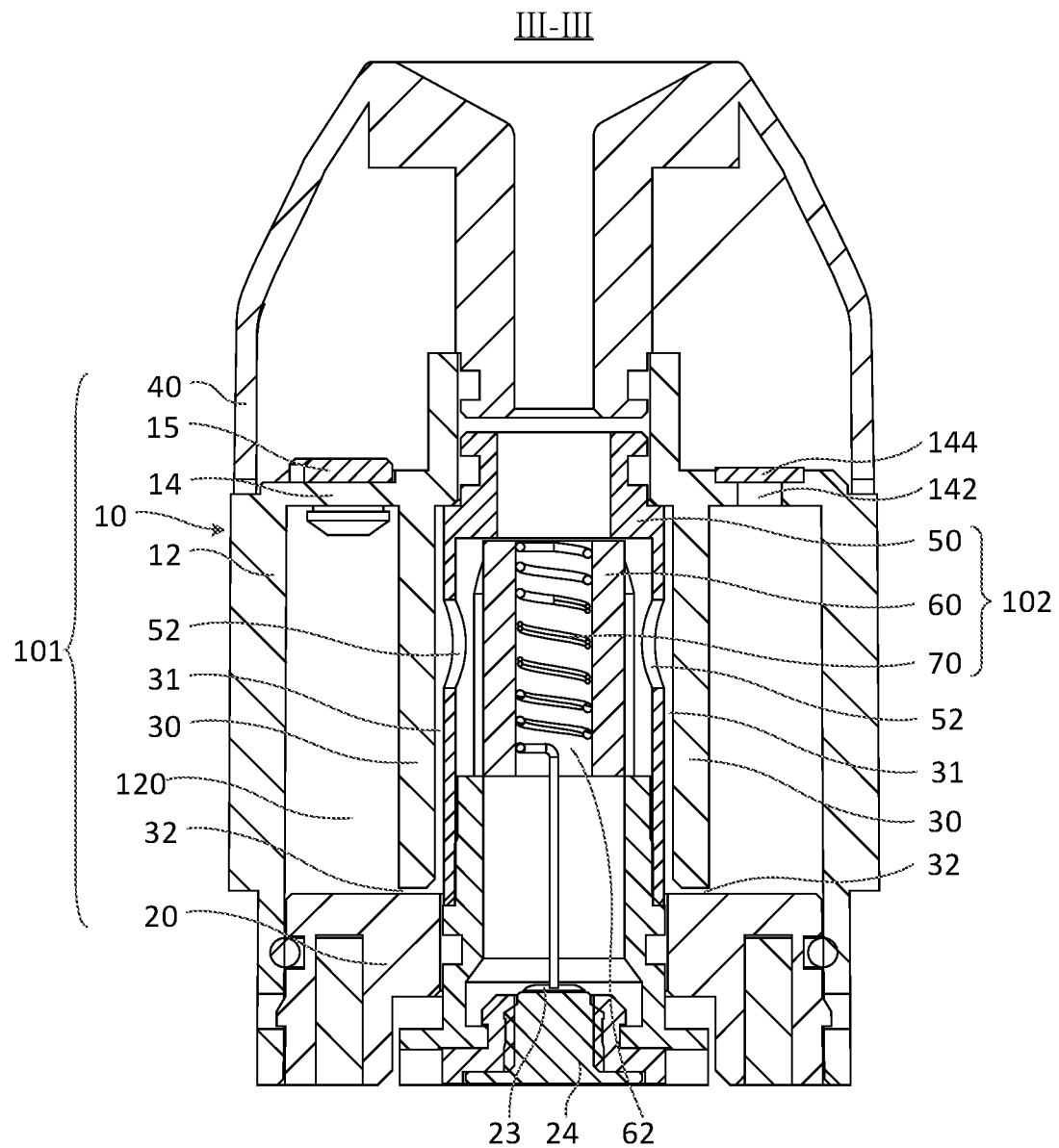
FIG. 3 is a first cross-sectional structural schematic view of the atomizer in direction III-III in FIG. 2.

An electronic atomizing device 300 is provided in this disclosure. FIG. 1 is a structural schematic view of an electronic atomizing device according to an embodiment of the present disclosure. FIG. 2 is a lateral structural view of an atomizer of the electronic atomizing device in FIG. 1. FIG. 3 is a cross-sectional structural schematic view of the atomizer in direction in FIG. 2.

The electronic atomizing device 300 may be used for atomizing the e-cigarette liquid. The electronic atomizing device 300 may include an atomizer 100 and a body assembly 200 connected to the atomizer 100. The atomizer 100 may be used for storing liquid and atomizing the liquid to form smoke that can be inhaled by a person. The liquid may be liquid matrix such as e-liquid, liquid medicine, etc. The body assembly 200 can be used to supply power to the atomizer 100 for atomizing the e-liquid and forming smoke.

In this embodiment, the case of using e-liquid as the liquids will be described in detail.

The atomizer 100 generally includes a liquid storage assembly 101 and an atomizing core assembly 102. The atomizing core assembly 102 can be arranged in the liquid storage assembly 101. The liquid storage assembly 101 can be used to store the e-liquid, the atomizing core assembly 102 can be used to atomize the e-liquid to form smoke.

Figure 5:
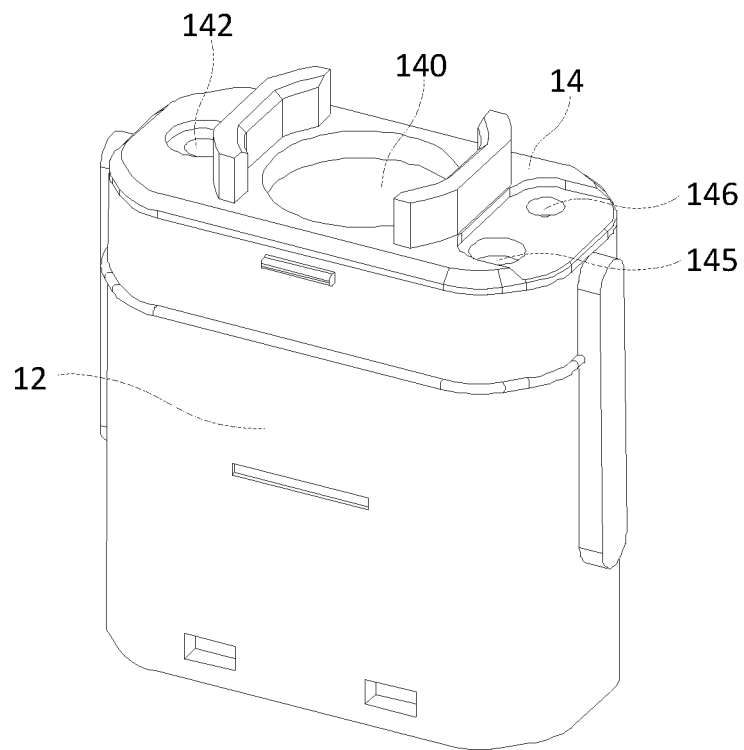
FIG. 5 is an axial side structural schematic view of a housing of the atomizer in FIG. 3.
Figure 6:
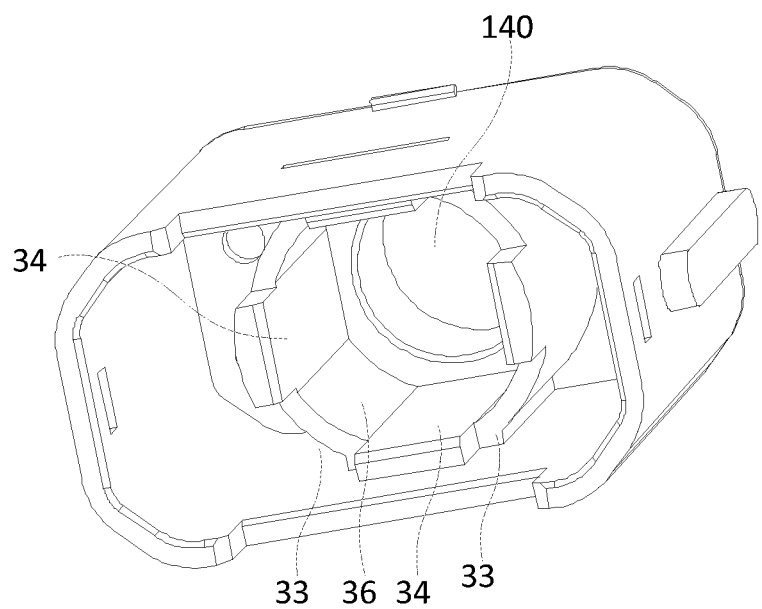
FIG. 6 is a structural schematic diagram of the housing and the inner wall of the atomizer in FIG. 3.

Specifically, the liquid storage assembly 101 includes a housing 10, an inner wall 30 and a cigarette holder 40. The housing 10 defines a liquid storage cavity 120 and a first assembling hole 140 (as shown in FIG. 5 and FIG. 6). The first assembling hole 140 can be used to receive an end of the atomizing core assembly 102. An inner wall 30 is arranged in the liquid storage cavity 120. The cigarette holder 40 covers the housing 10. The atomizing core assembly 102 is arranged in the liquid storage cavity 120, and has a liquid inlet 52. A capillary gap 31 capable of generating capillary action is defined between the inner wall 30 and an outer wall of the atomizing core assembly 102. When liquid level of the housing 10 below a position of the liquid inlet 52, the e-liquid stored in the storage assembly 101 may be guided to the liquid inlet 52 along the capillary gap 31. The e-liquid could be guided to the liquid inlet 52 and be atomized by the atomizing core assembly 102, therefore improving a utilization rate of the e-liquid and reducing waste of the e-liquid.

In some embodiments, the atomizing core assembly 102 and the liquid storage assembly 101 can be detachably connected, such that the atomizing core assembly 102 could be replace. Referring to FIG. 3, the atomizing core assembly 102 could be pulled out from the bottom side of the atomizer 100, so as to install a new atomizing core assembly 102 into the atomizer 100. When the atomizing core assembly 102 is needed to be replaced, a user could turn the atomizer 100 upside down, and pull out the atomizing core assembly 102, such that remaining e-liquid in the liquid storage cavity 120 could be placed on a side far away from the base 20 under gravity, and the inner wall could block the e-liquid, and the e-liquid cannot move into the atomizing core assembly 102. Therefore, the e-liquid remaining in the liquid storage cavity 120 cannot leak out due to blocking of the inner wall 30, thereby avoiding the e-liquid leakage during the replacement of the atomizing core assembly 102, improving user experience.

In this embodiment, referring to FIG. 3 and FIG. 5, the housing 10 includes a cylinder 12, a cover 14 and a base 20, the cover 14 is arranged on an end of the cylinder 12, and the base 20 is arranged on the other end of the cylinder 12. The cover 14, the cylinder 12 and the base 20 cooperatively define the liquid storage cavity 120. The liquid storage cavity 120 is used for storing e-liquid. The cover 14 defines the first assembling hole 140 communicating with the liquid storage cavity 120. The first assembling hole 140 is used to receive the end of the atomizing core assembly 102.

The cover 14 defines an air hole 142, and the air hole 142 communicates with the liquid storage cavity 120. A waterproof ventilated membrane 144 covers the air hole 142 for reducing a possibility of the e-liquid in the liquid storage cavity 120 leaking from the air hole 142, which could facilitate gas exchange between the liquid storage cavity 120 and atmosphere. As a result, air pressure in the liquid storage cavity 120 can be kept consistent with the atmospheric pressure, thereby improving an ability of the atomizer 100 to withstand higher temperatures. Therefore, intracavity temperature of the liquid storage cavity 120 will not excessively fluctuate and an unbalance between the intracavity pressure and atmospheric pressure will not happen. In this way, it is possible to avoid liquid leakage caused by excessively high air pressure in the liquid storage cavity 120, which is beneficial to reduce liquid leakage of the atomizer 100.

The cover 14 further defines a liquid injection hole 145 and a mounting hole 146, the liquid injection hole 145 and the mounting hole 146 are communicated with the liquid storage cavity 120.

Figure 7:
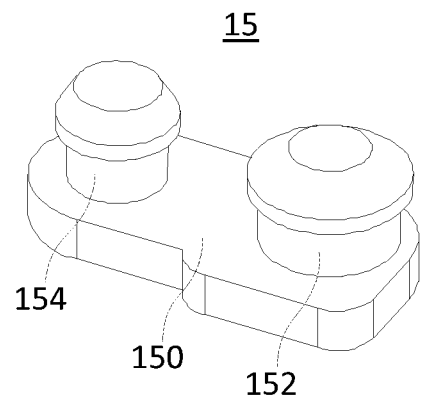
FIG. 7 is a structural schematic view of a sealing plug of the atomizer in FIG. 2.

Referring to FIG. 3 and FIG. 7, the liquid storage assembly 101 further includes a sealing plug 15. The sealing plug 15 includes a connecting cover plate 150. A first sealing column 152 and a second sealing column 154 are disposed on one side of the connecting cover plate 150. The first sealing column 152 is configured to seal off the liquid injection hole 145, and the second sealing column 154 is configured to seal off the mounting hole 146.

In some embodiments, the liquid injection hole 145 has a larger hole diameter than that of the mounting hole 146.

In this embodiment, the sealing plug 15 may be made of silicone material, plastic material, etc., the sealing plug 15 can be configured to block and seal off the first injection hole 145 and the mounting hole 146.

During a process of injecting liquid, liquid can be injected into the liquid storage cavity 120 through the liquid injection hole 145. The mounting hole 146 can communicate with the atmosphere and the liquid storage cavity 120. In this way, during the liquid injection process, the sealing plug 15 can rotate around sealed mounting hole 146 to expose unsealed liquid injection hole 145. The liquid can be injected into the liquid storage cavity 120 through the unsealed liquid injection hole, such that the sealing plug 15 does not need to be completely separated from the cover 14 during the process of injecting liquid, which can reduce a possibility of the sealing plug 15 being lost.

Figure 8:
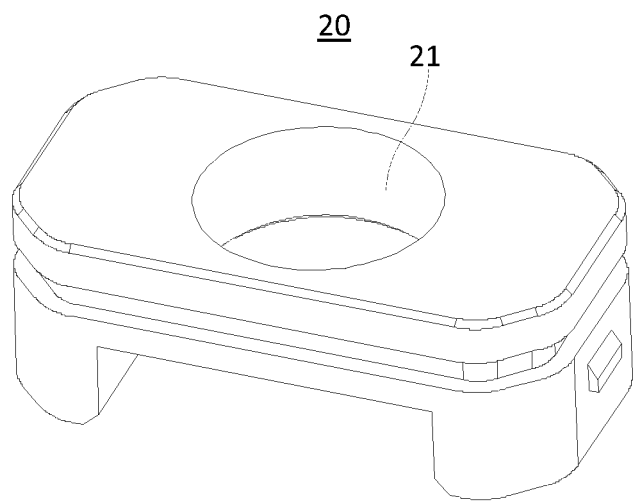
FIG. 8 is a first structural schematic view of a base of the atomizer in FIG. 2.

Referring to FIGS. 3 and 8, a base 20 is arranged at the other end of the cylinder 12 away from the cover 14. The base 20 is connected to the cylinder 12 in a sealing manner, the base 20 defines a second assembling hole 21 corresponding to the first assembling hole 140. The second assembling hole 21 is used to receive another end of the atomizing core assembly 102.

In this embodiment, the cylinder 12 and the cover 14 are formed of a single piece, and the base 20 is detachably connected to the cylinder 12. In other embodiments of the present disclosure, the cylinder 12 and the cover 14 also can be detachably connected and/or the base 20 and the housing 10 can be formed of a single piece.

In other embodiments, the housing 10 may be in a shape of an ellipse, a sphere, a cylinder, or a diamond, or the housing 10 may have a split combination structure. The housing 10 may include a spherical housing and a bottom cover. The bottom cover and the spherical housing are connected to form the liquid storage cavity 120. In other embodiments, the housing 10 may include a rectangular housing and a top cover. The rectangular housing and the top cover are connected to form the liquid storage cavity 120.

Figure 9:
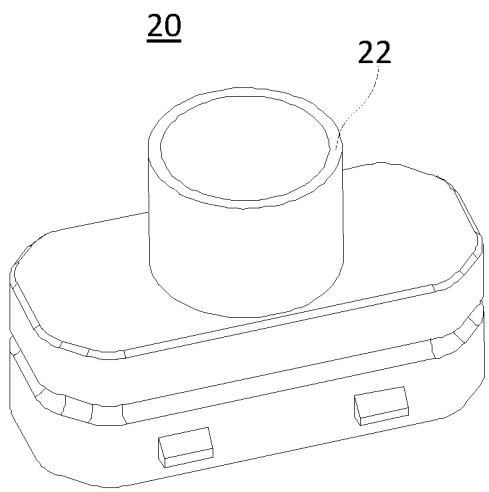
FIG. 9 is a second structural schematic view of a base of the atomizer in FIG. 2.
Figure 10:
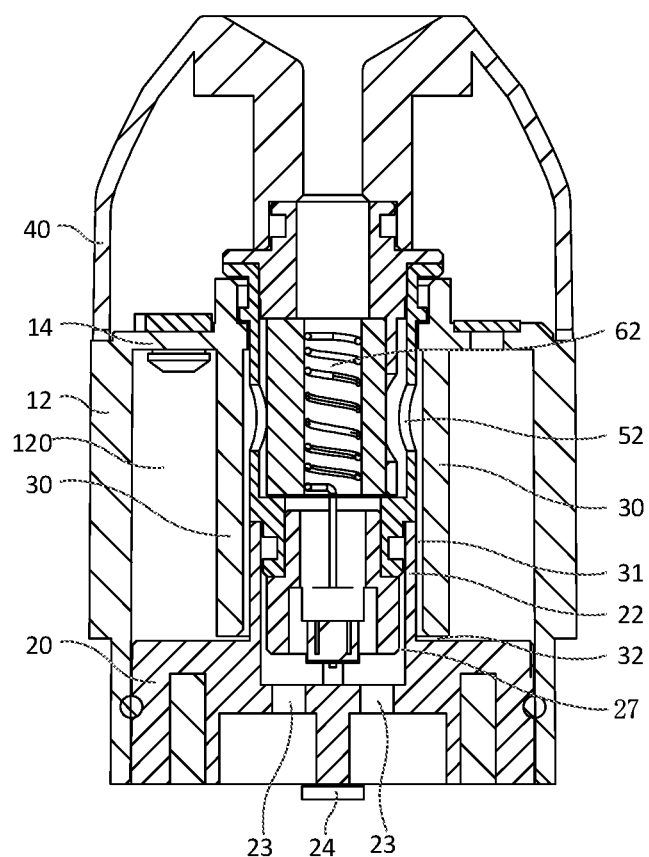
FIG. 10 is a second cross-sectional structural schematic view of the atomizer in direction VI-VI in FIG. 2.

In some embodiments, referring to FIG. 9 and FIG. 10, the atomizing core assembly 102 is installed from the first assembling hole 140 to the second assembling hole 21. A retaining ring 22 is arranged at the base 20 and around the second assembling hole 21. The inner wall 30 is located outside the retaining ring 22. The retaining ring 22 is further assembled and hermetically connected to the atomizing core assembly 102. The retaining ring 22 is configured to block the residual e-liquid in the liquid storage cavity 120, so as to reduce a possibility of the residual e-liquid entering the second assembling hole 21 and leaking out when the atomizing core assembly 102 is removed from one side of the cover 14.

The base 20 further defines an air inlet 23, and the base 20 include an electrode 24 electrically connected with the atomizing core assembly 102. The air inlet 23 is communicated with an atomizing cavity in the atomizing core assembly 102. Air entering the atomizing cavity from the air inlet 23 can carry smoke in the atomizing cavity to a human oral cavity.

In some embodiment, the atomizing core assembly 102 could be pulled out from the top side of the atomizer 100 (as shown in FIG. 10). When the atomizing core assembly 102 replacement operation is needed, the user could remove the cigarette holder 40 firstly, and then pull out the atomizing core assembly 102. In this embodiment, in order to prevent the e-liquid in the liquid storage cavity 120 from leaking out, a blocking member 27 could be arranged on the base 20 to prevent the e-liquid in the liquid storage cavity 120 from leaking out from air inlet 23 during the replacement process of the atomizing core assembly 102.

In other embodiments, referring to FIGS. 3, 5 and 8, the atomizing core assembly 102 is installed from the second assembling hole 21 to the first assembling hole 140. A retaining ring 22 is arranged on the cover 14 and around the first assembling hole 140. The inner wall 30 is located outside the retaining ring 22. The retaining ring 22 is used to block the residual e-liquid in the liquid storage cavity 120, so as to reduce a possibility of the residual e-liquid entering the first assembling hole 140 and leaking out when the atomizing core assembly 102 is removed from one side of the base 20.

The atomizing core assembly 102 defines an air inlet 23, the atomizing core assembly 102 includes an electrode 24, the air inlet 23 is communicated with an atomizing cavity of the atomizing core assembly 102, and the electrode 24 is electrically connected to an atomizing member 70 of the atomizing core assembly 102.

Referring to FIG. 3, the inner wall 30 is disposed in the liquid storage cavity 120 and a capillary gap 31 is defined between the inner wall 30 with the outer wall of the atomizing core assembly 102. The inner wall 30 is disposed corresponding to the liquid inlet 52, such that the capillary gap 31 can communicate with the liquid inlet 52. When the liquid level of the liquid storage cavity 120 is below the position of the liquid inlet 52, the liquid in the liquid storage cavity 120 can enter the liquid inlet 52 along the capillary gap 31 by the capillary action. Therefore, the residual e-liquid can flow into the liquid inlet 52 to be atomized by atomizing core assembly 102, which could improve the utilization rate of the e-liquid and reduce the waste of the e-liquid.

A gap 32 is defined between the base 20 and an end of the inner wall 30 facing the base 20. The gap 32 is in communication with the capillary gap 31. The thickness of the gap 32 is greater than or equal to 0.5 mm. The gap 32 is configured to allow the e-liquid in the liquid storage cavity 120 to pass through the capillary gap 31. The e-liquid can be guided to the liquid inlet 52 along the capillary gap 31 by the capillary action. Therefore, the e-liquid at the bottom of the liquid storage cavity 120 can flow into the liquid inlet 52 along the capillary gap 31, which could improve the utilization rate of the e-liquid and reducing the waste of the residue e-liquid. A width of the gap 32 can be greater than or equal to 0.5 mm, which could facilitate the e-liquid entering the capillary gap 31 from the gap 32.

The atomizing core assembly 102 defines the liquid inlet 52, and two ends of the atomizing core assembly 102 are respectively received the first assembling hole 140 and second assembling hole 21. Such that, the liquid inlet 52 can be located in the liquid storage cavity 120, and the e-liquid in the liquid storage cavity 120 can enters the atomizing core assembly 102 from the liquid inlet 52. The atomizing core assembly 102 also can be used to atomize the e-liquid to form smoke.

Specifically, referring to FIG. 3 or FIG. 10, the atomizing core assembly 102 includes a sleeve 50, a liquid absorbing member 60 and an atomizing member 70. The sleeve 50 may define a liquid inlet 52, the liquid absorbing member 60 can be disposed in the sleeve 50. An atomizing chamber 62 may be defined at center of the liquid absorbing member 60. The atomizing member 70 may be embedded in the atomizing chamber 62. The e-liquid can enter the sleeve 50 from the liquid inlet 52. The liquid absorbing member 60 could be a liquid absorbing cotton which could be used for absorbing the e-liquid and guiding the e-liquid to the atomizing part 70. The atomizing part 70 may be a heating wire, a ceramic atomizing core or the like which could atomize the e-liquid.

The sleeve 50 may define at least one liquid inlet 52. In this embodiment, the sleeve 50 defines a plurality of liquid inlets 52, and the plurality of liquid inlets 52 are communicated with the capillary gap 31.

The thickness of the capillary gap 31 between the inner wall 30 and the outer wall of the atomizing core assembly 102 ranges from 0.1 mm to 0.6 mm That is, the thickness of the capillary gap 31 defined between the inner wall 30 and the outer wall of the sleeve 50 is 0.1 mm to 0.6 mm Within this numerical range, the capillary gap 31 has a strong capillary action, which is beneficial for the e-liquid to be guided to the atomizing core assembly 102 along the capillary gap 31 for atomizing.

Figure 4:
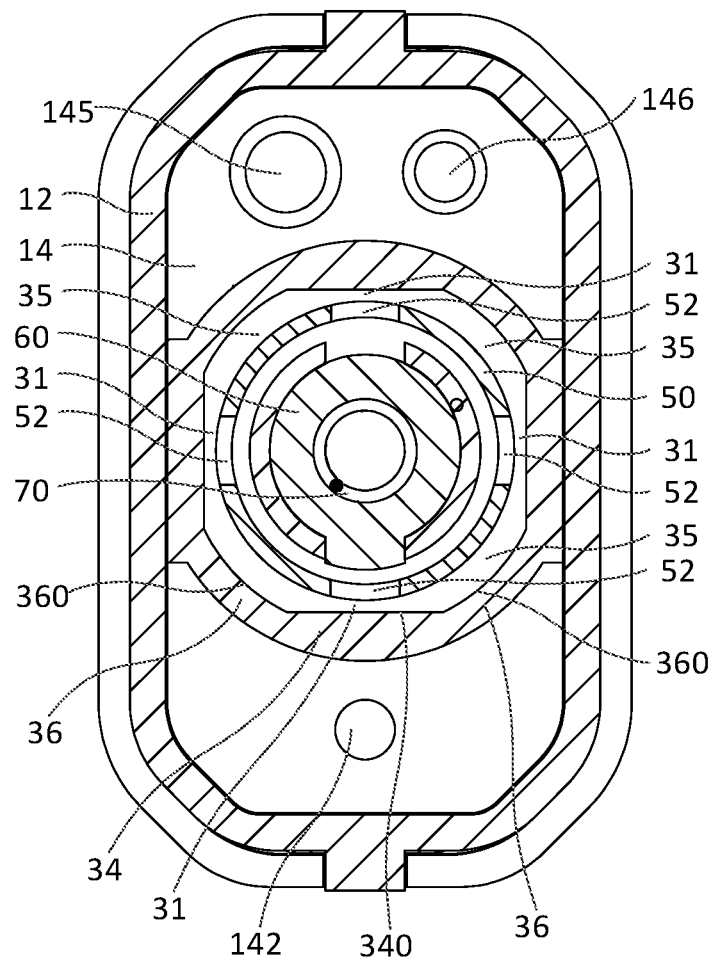
FIG. 4 is a first cross-sectional structural schematic view of the atomizer in direction IV-IV in FIG. 2.

In some embodiments, referring to FIG. 3 and FIG. 4, the inner wall 30 is connected to the cover 14 and/or the cylinder 12.

In at least one embodiment, the inner wall 30 and the inner side wall of the cover 14 and/or the cylinder 12 are formed of a single piece, which could simplify the assembling and manufacturing process of the housing 10 and the inner wall 30.

In at least one embodiment, the inner wall 30 is detachably connected to the inner side wall of the cover 14 and/or the cylinder 12. The inner wall 30 could be plugged in the inner side wall of the cover 14 and/or the cylinder 12, or the inner wall 30 can be fixed to the inner side wall of the cover 14 and/or the cylinder 12 by a fastener. Thereby, it is convenient to disassemble the inner wall 30 form the inner side wall of the cover 14 and/or the cylinder 12, such that cleaning or replacing the inner wall 30 could be more convenient.

In other embodiments, the inner wall 30 is connected to the atomizing core assembly 102, and arranged in the liquid storage cavity 120 when the atomizing core assembly 102 are received by the first assembling hole 140 and the second assembling hole 21.

In other embodiments, the inner wall 30 and the outer wall of the sleeve 50 may be formed of a single piece. In at least one embodiment, the inner wall 30 may be detachably connected to the outer wall of the sleeve 50, for example, by snap connection or by fasteners.

In other embodiments, the inner wall 30 also could be connected to the base 20 and arranged in the liquid storage cavity 120 when the base 20 covers the cylinder 12.

In at least one embodiment, the inner wall 30 and the base 20 may be formed of a single piece. In at least one embodiment, the inner wall 30 also may be detachably connected to the base 20, for example, by plug connection or by fasteners.

In some embodiments, referring to FIG. 3 or FIG. 10, the inner wall 30 could be connected to the housing 10 or the atomizing core assembly 102. The inner wall 30 could be suspended in midair relative to the base 20, and a gap 32 could be defined between the base 20 and an end of the inner wall 30 facing the base 20.

In other embodiments, referring to FIG. 6, a portion of the end of the inner wall 30 facing the base 20 is connected to the base 20, and another portion of the end of the inner wall 30 facing the base 20 defines a notch 33 to from the gap 32.

In at least one embodiment, the inner wall 30 is connected to the housing 10 or the atomizing core assembly 102. The end of the inner wall 30 facing the base 20 abuts against the base 20 or is plugged in the base 20. The notch 33 could form the gap 32 between the inner wall 30 and the base 20. In one embodiment, the end of the inner wall 30 facing the base 20 is detachably connected to the base 20. The notch 33 could form the gap 32 between the inner wall 30 and the base 20. In another embodiment, the notch 33 may be a hole defined on the end of the inner wall 30 facing the base 20, and the notch 33 is communicated with the capillary gap 31 and form the gap 32 between the base 20 and the end of the inner wall 30 facing the base 20.

In some embodiments, the inner wall 30 has a cylindrical shape and is sleeved on an outer circumference of the atomizing core assembly 102. The inner wall 30 may be connected to the housing 10, the base 20 or the atomizing core assembly 102.

Referring to FIGS. 3, 4 and 6, the inner wall 30 has a cylindrical shape, the inner wall 30 and the housing 10 are formed of a single piece, the inner wall 30 is suspended in midair relative to the base 20, and a gap 32 is defined between the inner wall 30 and the base 20.

The inner wall 30 comprises a first wall 34 and a second wall 36 formed of a single piece. The first wall 34 is corresponded to the liquid inlet 52, the capillary gap 31 is defined between the first wall 34 and the outer wall of the atomizing core assembly 102, a non-capillary gap 35 is defined between the second wall 36 and the outer wall of the atomizing core assembly 102. The non-capillary gap 35 is communicated with the capillary gap 31. A distance between the second wall 36 and the outer wall of the atomizing core assembly 102 is greater than that between the first wall 34 and the outer wall of the atomizing core assembly 102. That is, the thickness of the non-capillary gap 35 is greater than that of the capillary gap 31.

The capillary gap 31 may have a significant capillary action, and the e-liquid below the level of the liquid inlet 52 could be guided to the liquid inlet 52 by the capillary action. The non-capillary gap 35 may have no capillary action or has an insignificant capillary action. The thickness of the non-capillary gap 35 is quite large, the e-liquid could easily enter the non-capillary gap 35. The liquid level in the non-capillary gap 35 could be consistent with liquid level of the liquid storage cavity 120, and the liquid level in the non-capillary gap 35 changes along with the changing of the liquid level of the liquid storage cavity 120. Therefore, when the liquid level of the liquid storage cavity 120 is not lower than the position of the liquid inlet 52, the e-liquid could easily enter the liquid inlet 52 through the non-capillary gap 35. When the liquid level of the liquid storage cavity 120 is lower than the position of the liquid inlet 52, the e-liquid also could easily enter the capillary gap 31 through the non-capillary gap 35. The e-liquid could be guided to the liquid inlet 52 by the capillary action of the capillary gap 31, which is beneficial to improve the efficiency of the e-liquid entering the liquid inlet 52.

In this embodiment, the inner wall 30 includes a plurality of first wall 34 and a plurality of second wall 36, the plurality of first wall 34 and the plurality of second wall 36 are alternately arranged. The first wall 34 is correspond to the liquid inlets 52 of the atomizing core assembly 102, such that the e-liquid could be guide to the liquid inlets 52 by the capillary gap 31. The second wall 36 may be corresponded to part of the sleeve 50 between adjacent liquid inlets 52, or the first wall 34 and the second wall 36 are corresponded to different liquid inlets 52, or a same liquid inlet 52 is corresponded to the adjacent first wall 34 and the adjacent second wall 36.

The plurality of first wall 34 and the plurality of second wall 36 are arranged alternately at intervals. The plurality of first wall 34 and the plurality of second wall 36 are in a cylindrical integrated structure. Furthermore, a plurality of liquid inlets 52 are evenly arranged on the outer wall of the atomizing core assembly 102. The e-liquid could be evenly guided to the plurality of liquid inlets 50 along the capillary gap 31 between the inner wall 30 and the outer wall of the atomizing core assembly 102, thereby improving liquid inletting process stability of the atomizing core assembly 102 and improving the atomizing efficiency of the atomizer 100.

Furthermore, one end of the first wall 34 facing the base 20 protrudes out of the second wall 36, and the notch 33 is defined between the second wall 36 and portions of two adjacent first walls 34 protruding out of the second wall 36. The gap 32 is defined between the first wall 34 and the base 20, the notch 33 is used to facilitate the e-liquid to enter the non-capillary gap 35 and the capillary gap 31, thereby improving the liquid inlet efficiency.

In at least one embodiment, the inner wall 30 may also include a first wall 34 and a second wall 36, and the first wall 34 and the second wall 36 are arranged in a cylindrical shape, which has been described above in detail, and will not be repeated here.

In one embodiment, the first wall 34 has a flat surface 340 facing the outer wall of the atomizing core assembly 102, the capillary gap 31 defined between the flat surface 340 and the outer wall of the atomizing core assembly 102 is non-uniform. The second wall 36 has a curved surface 360 facing the outer wall of the atomizing core assembly 102, the non-capillary gap 35 defined between the curved surface 360 and the outer wall of the atomizing core assembly 102 is uniform.

In one embodiment, the outer wall of the atomizing core assembly 102 has a cylindrical shape. In other words, the outer wall of the sleeve 50 has a cylindrical shape, and the inner wall 30 having a cylindrical shape is sleeved on the outer periphery of the sleeve 50. The side surface of the first wall 34 facing the outer wall of the sleeve 50 is a flat surface 340, the capillary gap 31 defined between the flat surface 340 and the outer wall of the sleeve 50 is non-uniform. The side surface of the second wall 36 facing the outer wall of the sleeve 50 is a curved surface 360, the non-capillary gap 35 formed between the curved surface 360 and the outer wall of the sleeve 50 is uniform.

Specifically, the first wall 34 is corresponded to the liquid inlet 52, the capillary gap 31 is defined between the flat surface 340 and the curved surface 360. The thickness of the capillary gap 31 gradually decreases from a contacting edge where the flat surface 340 is in contact with the curved surface 360 to middle of the flat surface 340. The capillary action generated by the capillary gap 31 gradually increases from the contacting edge where the flat surface 340 is in contact with the curved surface 360 to the middle of the flat surface 340, thereby the e-liquid could easily flow into the capillary gap 31 from the non-capillary gap 35, and the e-liquid at the edge of the capillary gap 31 could easily flow to the middle of the capillary gap 31. Since the middle of the capillary gap 31 has stronger adhesion to the e-liquid, the e-liquid could enter the liquid inlet 52 by the capillary action more easily.

In this embodiment, the curved surface 360 is parallel to arc surface of the sleeve 50 to form the uniform non-capillary gap 35. The non-capillary gap 35 may have no capillary action, and the liquid level in the non-capillary gap 35 is almost consistent with the liquid level of the liquid storage cavity 120. The liquid level in the non-capillary gap 35 also changes with the change of the liquid level of the liquid storage cavity 120.

In other embodiments, the inner wall 30 has a cylindrical shape. The inner wall 30 may be connected to the base 20 or the atomizing core assembly 102. The uniform capillary gap 31 may be formed between the first wall 34 and the outer wall of the atomizing core assembly 102. A uniform non-capillary gap 35 or a non-uniform non-capillary gap 35 could be defined between the second wall 36 and the outer wall of the atomizing core assembly 102.

In other embodiments, a plurality of inner walls 30 may be arranged around the atomizing core assembly 102 at intervals, and each of the inner walls 30 corresponds to a liquid inlet 52.

Figure 11:
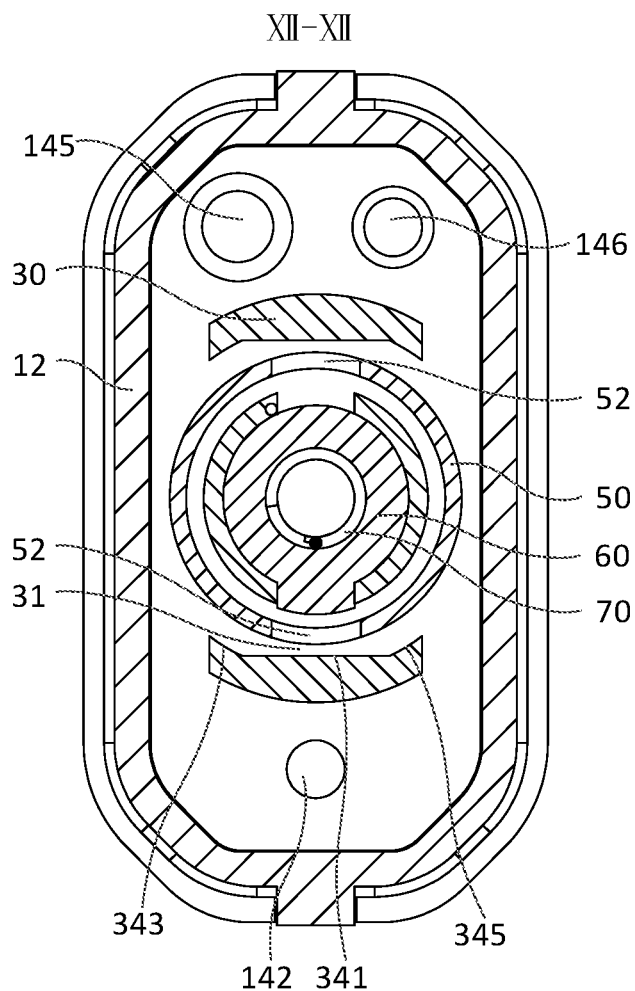
FIG. 11 is a second cross-sectional structural schematic view of the atomizer in direction VII-VII in FIG. 2.
Figure 12:
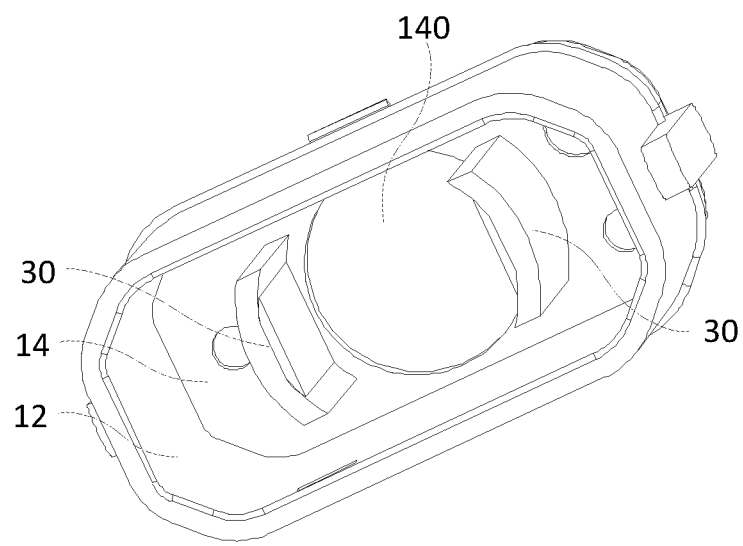
FIG. 12 is a structural schematic diagram of the housing and the inner wall of the atomizer in FIG. 10.

Referring to FIG. 10, FIG. 11 and FIG. 12, the inner walls 30 and the cover 14 could be formed of a single piece, the inner wall 30 could be suspended in midair relative to the base 20, and a gap 32 is defined between the inner walls 30 and the base 20.

A side surface of the inner wall 30 facing the atomizing core assembly 102 comprises a capillary plane 341, a first cambered surface 343 connected to one side of the capillary plane 341 and a second cambered surface 345 connected to the other side of the capillary plane 341. The first cambered surface 343 and the second cambered surface 345 are bent inward relative to the capillary plane 341. The capillary gap 31 defined between the capillary plane 341 and the outer wall of the atomizing core assembly 102 is non-uniform. The first cambered surface 343 and the second cambered surface 345 are used to reduce fluctuation interference of the e-liquid in the liquid storage cavity 120 on the capillary gap 31, thereby reducing the fluctuation of the e-liquid due to blocking of the first cambered surface 343 and the second cambered surface 345, and reducing the interference of capillary action generated by the capillary gap 31.

The outer wall of the sleeve 50 may have a cylindrical shape, and the capillary gap 31 defined between the capillary plane 341 and the arc surface of the sleeve 50 is non-uniform. The thickness of the capillary gap 31 may gradually decrease from the edge where the capillary plane 341 is in contact with the first cambered surface 343 and the second cambered surface 345 to the middle of the capillary plane 341.

In other embodiments, the plurality of inner walls 30 may be connected to the base 20 or the atomizing core assembly 102. A uniform capillary gap 31 may be defined between the inner wall 30 and the outer wall of the atomizing core assembly 102.

Figure 13:
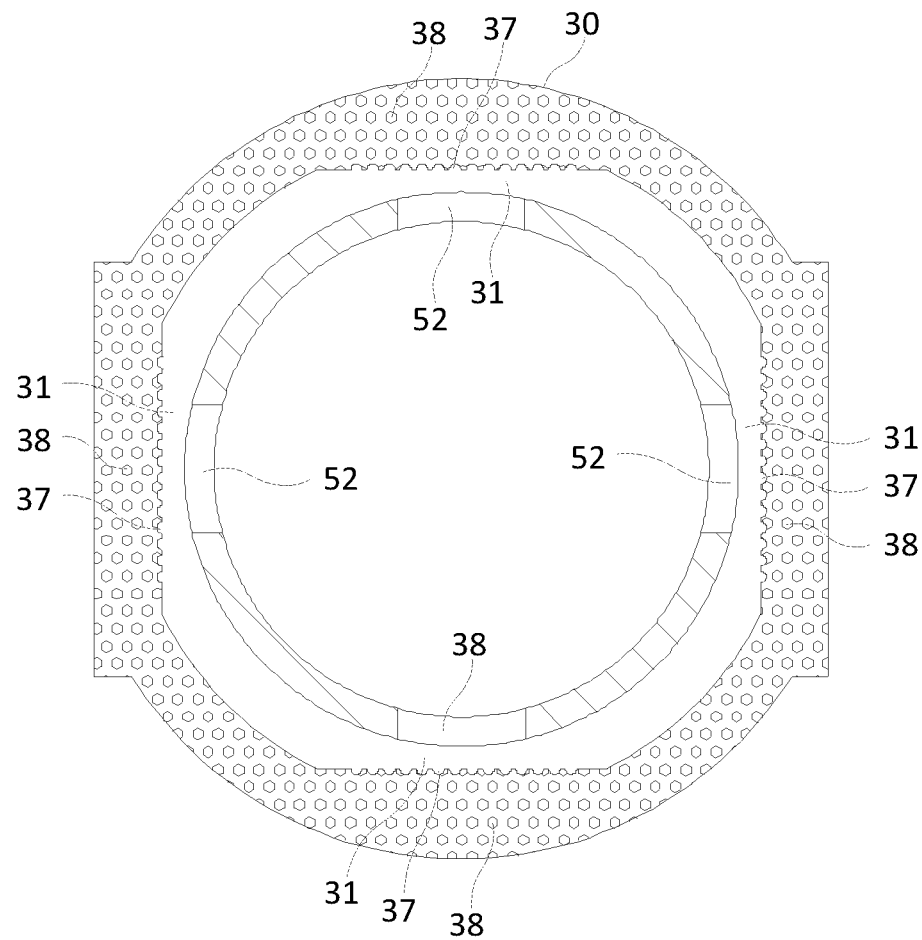
FIG. 13 is a cross-sectional structural schematic view of an inner wall and sleeve of the atomizer in FIG. 4.

Further, referring to FIG. 13, a plurality of capillary grooves 37 capable of generating capillary action are defined on side surface of the inner wall 30 facing the outer wall of the atomizing core assembly 102. The capillary grooves 37 are communicated with the capillary gap 31, and the e-liquid could be guided to the liquid inlet 52 along the capillary grooves 37 and the capillary gap 31. The capillary groove 37 could further increase a contacting area between the e-liquid and the capillary gap 31, thereby the capillary gap 31 has a stronger tension and adsorption force on a surface of the smoke liquid, and generating a stronger capillary action.

The capillary groove 37 may be defined in a straight line along the inner wall 30 from the side where the base 20 is located toward the liquid inlet 52, or the capillary groove 37 is tortuously arranged along the inner wall 30 from the side where the base 20 is located toward the liquid inlet 52.

And/or, a plurality of capillary pores 38 capable of generating capillary action are defined on the inner wall 30. The capillary pores 38 may be communicated with the capillary gaps 31, and the capillary pores 38 may be configured to guide the liquid in the liquid storage cavity 120 to the liquid inlet 52.

For example, A plurality of capillary pores 38 are fully distributed inside the inner wall 30, such that the entire inner wall 30 and the capillary gap 31 both have capillary actions, thereby increasing guiding effect of capillary action and improving the liquid guiding efficiency greatly.

The plurality of capillary pores 38 may be evenly arranged inside the inner wall 30, or the plurality of capillary pores 38 may be randomly arranged inside the inner wall 30. The plurality of capillary pores 38 could be used to guide the e-liquid to the liquid inlet 52. Besides, the plurality of capillary pores 38 also could be communicated with each other. A liquid inlet port of the capillary pore 38 could be located on the side of the inner wall 30 away from the atomizing core assembly 102. The liquid inlet port of the capillary pore 38 also could be located on the side of the inner wall 30 facing the base 20. A liquid outlet port of the capillary pore 38 could be located on the side of the inner wall 30 facing the atomizing core assembly 102, and at least part of the liquid outlet port of the capillary pore 38 could be arranged corresponding to the liquid inlet port 52.

Figure 14:
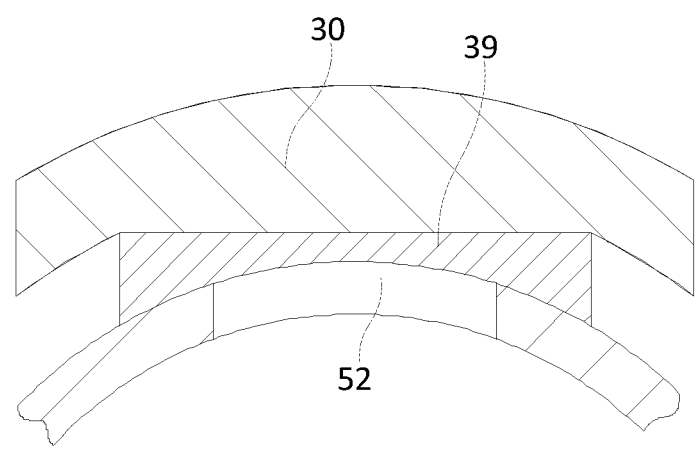
FIG. 14 is another cross-sectional structural schematic view of an inner wall and sleeve of the atomizer in FIG. 11.

In at least one embodiment, referring to FIG. 14, the side of the inner wall 30 facing the atomizing core assembly 102 is provided with a capillary element 39, the capillary element 39 is used to guide the e-liquid located in the liquid storage cavity 120 to the inlet aperture 52.

The capillary element 39 may be made of cotton, sponge, etc., and the capillary element 39 is capable of guiding the e-liquid at a low liquid level to the liquid inlet 52 at a high position.

Figure 15:
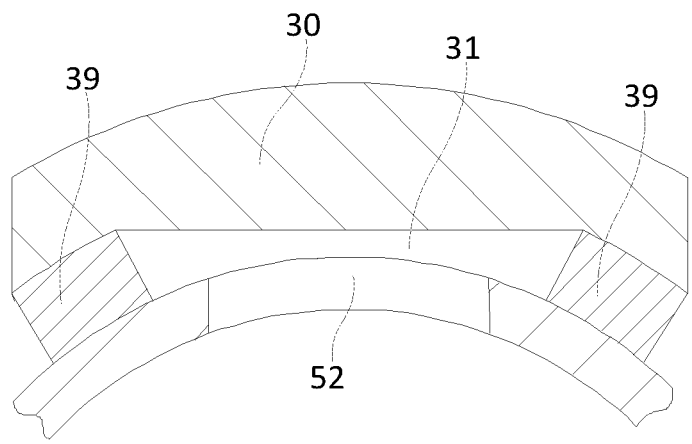
FIG. 15 is another cross-sectional structural schematic view of an inner wall and sleeve of the atomizer in FIG. 11.

As shown in FIG. 14, the capillary element 39 may be filled between the inner wall 30 and the outer wall of the atomizing core assembly 102. The capillary element 39 connected to the liquid inlet 52 extends to the bottom of the liquid storage cavity 120. In another embodiment, as shown in FIG. 15, two capillary elements 39 are disposed on one edge of the inner wall 30 and respectively arranged at two sides of the capillary gap 31 to enhance the capillary action and avoid the fluctuation influence of the e-liquid on the capillary action.

Being different from the prior art, this disclosure discloses an atomizer, a liquid storage assembly of the atomizer, and an electronic atomizing device. A liquid storage cavity is defined in a housing, the housing defines a first assembling hole, a liquid inlet of the atomizing core assembly assembled in the first assembling hole is arranged in the liquid storage cavity. An inner wall is arranged in the liquid storage cavity. A capillary gap capable of generating capillary action is defined between the inner wall and an outer wall of the assembled atomizing core assembly. The inner wall corresponds to the liquid inlet. The capillary gap communicates with the liquid inlet. When liquid level in the liquid storage cavity is lower than the position of the liquid inlet, the liquid in the liquid storage cavity can enter the liquid inlet along the capillary gap by capillary action. E-liquid can enter the liquid inlet and is able to be atomized by the atomizing core assembly, thereby improving the utilization rate of the liquid in the liquid storage cavity, and reducing the residual quantity of the liquid in the liquid storage cavity, and a risk of dry burning of the atomizing core assembly also can be avoided. Therefore, in the present disclosure, the liquid below the liquid inlet of the atomizing core assembly can be guided to the liquid core assembly, the utilization rate of liquid in the liquid storage cavity can be improved, and the risk of dry burning of the atomizer can also be effectively reduced.

The embodiments of the present disclosure have been described in detail above. Specific examples have been used herein to explain the principles and implementation of the present disclosure. The descriptions of the embodiments are only to help understand the method of the present disclosure and core ideas. For those skilled in the art, there will have a change in the specific embodiments and the scope of present disclosure according to the idea of the present disclosure. In summary, the content of the present specification should not be construed as limiting the present disclosure.

What is claimed is:

1. A liquid storage assembly for an atomizer, the atomizer comprising an atomizing core assembly having an outer wall, the outer wall having a liquid inlet, the liquid storage assembly comprising:
    a housing, defining a liquid storage cavity and a first assembling hole and comprising a base, wherein the base is disposed at an end of the liquid storage cavity away from the first assembling hole, wherein the first assembling hole is configured to receive an end of the atomizing core assembly;
    an inner wall, arranged in the liquid storage cavity, configured to sleeve around the atomizing core assembly, wherein a capillary gap is defined between the inner wall and an outer wall of the atomizing core assembly, a gap communicating with the capillary gap is defined between a portion of the base located at the end of the liquid storage cavity and an end of the inner wall facing the base, and the capillary gap is configured to guide liquid in the liquid storage cavity to flow from the gap to pass through the liquid inlet.

2. The liquid storage assembly according to claim 1, wherein a thickness of the capillary gap ranges from 0.1 mm to 0.6 mm.

3. The liquid storage assembly according to claim 1, wherein the housing further comprises a cylinder and a cover, wherein the cover is arranged on an end of the cylinder, the base is arranged on the other end of the cylinder; the liquid storage cavity is defined by the cover, the cylinder and the base; the cover defines the first assembling hole, the base defines a second assembling hole configured to receive another end of the atomizing core assembly.

4. The liquid storage assembly according to claim 3, wherein the inner wall is configured to connect to the cover and/or the cylinder; or
    the inner wall is connected to the atomizing core assembly and arranged in the liquid storage cavity when the atomizing core assembly are received in the first assembling hole and the second assembling hole; or
    the inner wall is connected to the base and arranged in the liquid storage cavity when the base seals the cylinder.

5. The liquid storage assembly according to claim 3, wherein the gap has a height greater than or equal to 0.5 mm.

6. The liquid storage assembly according to claim 5, wherein the inner wall is suspended in midair relative to the base, and the gap is defined between the base and the end of the inner wall facing the base; or
    a portion of the end of the inner wall facing the base is connected to the base, another portion of the end of the inner wall facing the base defines a notch to form the gap.

7. The liquid storage assembly according to claim 3, wherein a retaining ring is arranged at the base and around the second assembling hole, or the retaining ring is arranged at the cover and around the first assembling hole; the inner wall is arranged outside the retaining ring, and the retaining ring is configured connect to the atomizing core assembly.

8. The liquid storage assembly according to claim 1, wherein the inner wall has a cylindrical shape and is sleeved on outer circumference of the atomizing core assembly.

9. The liquid storage assembly according to claim 8, wherein the inner wall comprises at least one first wall and at least one second wall formed of a single piece, the at least one first wall is corresponded to the liquid inlet, the capillary gap is defined between the at least one first wall and an outer wall of the atomizing core assembly, a non-capillary gap is defined between the at least one second wall and the outer wall of the atomizing core assembly, the non-capillary gap communicates with the capillary gap; and a distance between the at least one second wall and the outer wall of the atomizing core assembly is greater than that between the at least one first wall and the outer wall of the atomizing core assembly.

10. The liquid storage assembly according to claim 9, wherein the number of the at least one first wall is more than one, the number of the at least one second wall is more than one, the more than one first walls and the more than one second walls are arranged alternately at intervals, the more than one first walls are corresponded to the liquid inlet of the atomizing core assembly, one end of the each of the more than one first walls facing the base protrudes out of the more than one second walls, and a notch is defined by portions of two adjacent first walls of the more than one first walls and one of the more than one second walls between the two adjacent first walls.

11. The liquid storage assembly according to claim 10, wherein each of the more than one first walls has a flat surface facing the outer wall of the atomizing core assembly, the capillary gap defined between the flat surface and the outer wall of the atomizing core assembly is non uniform, each of the more than one second walls has a curved surface facing the outer wall of the atomizing core assembly, the non-capillary gap defined between the curved surface and the outer wall of the atomizing core assembly is uniform.

12. The liquid storage assembly according to claim 1, wherein the inner wall comprises a plurality of inner sub-walls, the plurality of inner sub-walls are arranged around the atomizing core assembly at intervals.

13. The liquid storage assembly according to claim 12, wherein a side surface of the inner wall facing the atomizing core assembly comprises a capillary plane, a first cambered surface connected to one side of the capillary plane and a second cambered surface connected to the other side of the capillary plane, the first cambered surface and the second cambered surface are bent inwards relative to the capillary plane, and the capillary gap is defined between the capillary plane and the outer wall of the atomizing core assembly is non-uniform.

14. The liquid storage assembly according to claim 1, wherein a plurality of capillary grooves communicate with the capillary gap are defined on a side surface of the inner wall facing the outer wall of the atomizing core assembly; and/or a plurality of capillary pores communicate with the capillary gap are defined on the inner wall, and the plurality of capillary pores are configured to guide the liquid in the liquid storage cavity to the liquid inlet.

15. The liquid storage assembly according to claim 1, wherein a capillary element is arranged on a side of the inner wall facing the atomizing core assembly to guide the liquid in the liquid storage cavity to the liquid inlet.

16. The liquid storage assembly according to claim 15, wherein the capillary element is filled between the inner wall and the outer wall of the atomizing core assembly, connected to the liquid inlet, and extending to a bottom of the liquid storage cavity; or the capillary element is arranged on an edge of the inner wall and arranged at both sides of the capillary gap respectively.

17. The liquid storage assembly according to claim 1, wherein the housing further defines an air hole communicating with the liquid storage cavity, the air hole is covered with a waterproof ventilated membrane.

18. The liquid storage assembly according to claim 1, wherein the housing further defines a liquid injection hole and a mounting hole;

the liquid storage assembly further comprises a sealing plug, wherein the sealing plug comprises a connection cover plate, a first sealing column and a second sealing column; both the first sealing column and the second sealing column are arranged on one side of the connection cover plate, the first sealing column is configured to seal off the liquid injection hole, the second sealing column is configured to seal off the mounting hole.

19. An atomizer, comprising:
an atomizing core assembly, having an outer wall and the outer wall defining a liquid inlet; and
a liquid storage assembly comprising:
  a housing, defining a liquid storage cavity and a first assembling hole and comprising a base, wherein the base is disposed at an end of the liquid storage cavity away from the first assembling hole, wherein the first assembling hole is configured to receive an end of the atomizing core assembly; and
  an inner wall, arranged in the liquid storage cavity, configured to sleeve around the atomizing core assembly, wherein a capillary gap is defined between the inner wall and the outer wall of the atomizing core assembly, a gap communicating with the capillary gap is defined between a portion of the base located at the end of the liquid storage cavity and an end of the inner wall facing the base, and the capillary gap is configured to guide liquid in the liquid storage cavity to flow from the gap to pass through the liquid inlet;
wherein the atomizing core assembly is arranged in the liquid storage cavity,
when liquid level in the liquid storage cavity is lower than a position of the liquid inlet, liquid in the liquid storage cavity enters the liquid inlet along the capillary gap.

20. An electronic atomizing device comprising:
a body component; and
an atomizer comprising:
  an atomizing core assembly, having an outer wall and the outer wall defining a liquid inlet; and
  a liquid storage assembly comprising:
    a housing, defining a liquid storage cavity and a first assembling hole and comprising a base, wherein the base is disposed at an end of the liquid storage cavity away from the first assembling hole, wherein the first assembling hole is configured to receive an end of the atomizing core assembly, and
    an inner wall arranged in the liquid storage cavity, configured to sleeve around the atomizing core assembly, wherein a capillary gap is defined between the inner wall and the outer wall of the atomizing core assembly, a gap communicating with the capillary gap is defined between a portion of the base located at the end of the liquid storage cavity and an end of the inner wall facing the base, and the capillary gap is configured to guide liquid in the liquid storage cavity to flow from the gap to pass through the liquid inlet;
    wherein the atomizing core assembly is arranged in the liquid storage cavity, when liquid level in the liquid storage cavity is lower than a position of the liquid inlet, liquid in the liquid storage cavity enters the liquid inlet along the capillary gap;

wherein the body component is electrically connected to the atomizer to supply power to the atomizer.

* * * * *